United States Patent [19]

Strobel

[11] 4,277,462

[45] Jul. 7, 1981

[54] METHOD FOR TREATING DUTCH ELM DISEASE USING *P. SYRINGAE*

[75] Inventor: Gary A. Strobel, Bozeman, Mont.

[73] Assignee: Endowment and Research Foundation at Montana State University, Bozeman, Mont.

[21] Appl. No.: 95,448

[22] Filed: Nov. 19, 1979

[51] Int. Cl.[3] ...................... A01N 63/00; A01N 63/02

[52] U.S. Cl. ...................................... 424/93; 424/115; 435/170; 435/874

[58] Field of Search .................. 424/115, 93; 435/170, 435/874

[56] References Cited

U.S. PATENT DOCUMENTS 3,155,585 11/1964 De Vay .............................. 424/115

OTHER PUBLICATIONS

Myers et al., Proc. Amer. Phytopathol. Soc., vol. 12, (1978), p. 350.

Campana, Proc. Amer. Phytopathol Soc., vol. 3, (1976), p. 266.

De Vay et al., Phytopathology, vol. 58, (1968), pp. 95-101.

Sinden et al., Physicol. Pl. Path., vol. 1, (1971), pp. 199-213.

Gross et al., J. Appl. Bact., vol. 43, (1977), pp. 453-463.

De Vay et al., Phytopathology, vol. 52, (1962), p. 360.

Gross et al., Phytopathology, vol. 67, (1977), pp. 475-483.

Annual Meeting of American Phytopathological Society, Aug. 1978: Tucson, Arizona (oral presentation) by D. F. Myers.

*Primary Examiner*—Richard Raymond

*Attorney, Agent, or Firm*—Lowe, King, Price & Becker

[57] ABSTRACT

A novel method for treating Dutch elm disease by use of a certain strain of *Pseudomonas syringae*. This method includes the step of injecting this microorganism into an elm tree. Also disclosed is a process for isolating the antimycotic substance formed by the microorganism and the antimycotic substance itself.

19 Claims, No Drawings

METHOD FOR TREATING DUTCH ELM DISEASE USING *P. SYRINGAE*

TECHNICAL FIELD

This invention relates to the treatment of Dutch elm disease.

BACKGROUND ART

Dutch elm disease, caused by *Ceratocystic ulmi* (Buisman) C. Moreau, has killed millions of American elms since its first reported occurrence in the United States in 1930. The economic loss due to Dutch elm disease is estimated to be several billion dollars. Recommended control strategies for this disease have included destruction of vectors by sanitation and insecticide sprays, soil treatments to prevent root graft transmission, protective and therapeutic treatments with systemic fungicides, intensive surveillance and eradicative pruning, and resistant varieties of elm. While a single valuable tree might be protected by a combination of one or more of these strategies at a cost of several hundred dollars per year, no single control procedure has been completely effective.

Until recently, biological control of plant diseases has been directed more towards root diseases than disease of aerial plant parts, such as Dutch elm disease. Nevertheless, biological control of *Fomes annosus* (Fr.) Cke in the stumps of Scots pine by a second basidiomycete, *Peniophora gigantea* (Fr.) Masse, is an example of a very successful biological control involving an aerial plant part. Biological control of Dutch elm disease has been directed at the elm bark beetle vector and at the saprophytic stage of *C. ulmi.*

It is known that certain strains of *Pseudomonas syringae* produce broad spectrum antibiotics that are effective on a number of pathogenic bacteria and fungi when tested in vitro. This type of art is illustrated by U.S. Pat. No. 3,155,585 to De Vay; J. E. De Vay et al, *Phytopathology,* 58: 95–101 (1968); S. L. Sinden et al, *Physiol. Plant Pathol.,* 1: 199–213 (1971); D. Gross and J. E. De Vay, *Proc. Amer. Phytopathol. Soc.* 3: 269–270 (1976); D. C. Gross et al, *J. Appl. Bact.,* 43: 453–463 (1977); J. E. De Vay and G. A. Strobel, *Phytopathology,* 52: 360 (1962); and D. C. Gross and J. E. De Vay, *Phytophathology,* 67: 475–483 (1977). U.S. Pat. No. 3,155,585 also shows an in vivo effect in certain fruit trees of the antibiotic material formed by *P. syringae.*

The use of nystatin, an antifungal agent, to arrest Dutch elm disease in the tree is known. Exemplary of this type of prior art is R. J. Campana, *Proc. Amer. Phytopathol. Soc.,* 3: 266 (1976). Also, it is known that certain strains of *P. syringae* exert an antimycotic effect against *C. ulmi* when tested in vitro. This type of prior art is illustrated by D. F. Myers, D. C. Sands and G. A. Strobel, *Proc. Amer. Phytopathol. Soc.,* 12: 202 (1978).

However, this and the other prior art of which I am aware is deficient as failing to provide a method for treating Dutch elm disease that requires a single control procedure. Furthermore, this prior art fails to provide a single treatment procedure for the treatment of Dutch elm disease since retreatment is required.

DISCLOSURE OF THE INVENTION

It is accordingly one object of the present invention to provide a method for treating Dutch elm disease that requires only a single control procedure, that is, it does not require a combination of control strategies.

A further object of the present invention is to provide a method for treating Dutch elm disease that requires only a single treatment, that is, retreatment is not necessary.

Other objects and advantages of the present invention will become apparent as the description thereof proceeds.

In satisfaction of the foregoing objects and objectives, there is provided by this invention a method for treating Dutch elm disease. This method includes the step of applying a Dutch elm disease-controlling amount of *P. syringae* NRRL B-12050 to an elm tree.

BEST MODE FOR CARRYING OUT THE INVENTION

The method of the present invention is carried out by applying a Dutch elm disease-controlling amount of *P. syringae* NRRL B-12050 to an elm tree. The *P. syringae* is an oxidase negative, fluorescent pseudomonad of the *P. syringae* taxonomic group. This strain forms an antimycotic substance. This microorganism was obtained from D. C. Sands of Montana State University and has been designated DC 27+ in the culture collection of Montana State University. A culture thereof has been placed on permanent deposite with the culture collection of the Northern Utilization Research and Development Division (formerly Northern Regional Research Laboratory) of the U.S. Department of Agriculture and has been assigned Accession No. NRRL B-12050.

The *P. syringae* is maintained routinely in sterile distilled water and is re-isolatable at about 28° C. in the dark, on potato dextrose agar (PDA) plates or on medium B of E. O. King et al in *J. Lab. Clin. Med.,* 44: 301–307 (1954), the pertinent portion of this publication being hereby incorporated by reference into this application.

The *P. syringae* is applied to the elm by injection, with a sufficient amount of the *P. syringae* being in the range of about $10^8$ to $10^{11}$ total cells or in the range of about $10^8$ to $10^9$ living cells. Suitably, the *P. syringae* is injected in an aqueous vehicle containing Dye's salts supplemented with 1% glucose. Dye's salts are disclosed in D. W. Dye, *N. Z. J. Sci.,* 6: 495–506 (1963), which is hereby incorporated by reference into this application.

One method for carrying out the injection is a gravity flow method. This method is suitable for use in smaller elm trees. In this method, the *P. syringae* in suitably about 1 liter of Dye's salts supplemented with 1% glucose, is injected into an elm by drilling four to six holes, 11 cm in diameter and 2.5 cm deep, into the base of the elm, by fitting these holes with a plastic hosing network attached to a 1 liter plastic bottle containing this 1 liter mixture, and placing the plastic bottle about 1 m above the ground. Uptake is complete when the bottle is empty, with about 12 to 36 hours being sufficient. An alternative method is pressure injection. This method is used for larger elm trees. A pressure of about 10 lbs. is suitable. For pressure injection, there is used about 4 to 5 times the number of *P. syringae* cells in 60 liters of water containing about 4 liters of Dye's salts supplemented with 1% glucose. This mixture is injected into the elm via 20 to 30 T's, into root flares 20 cm below the ground. Injection of the 60 liter volume takes about 24 hours, with a higher pressure requiring a shorter time and a lower pressure requiring a longer time. When injection of the 60 liter solution is complete, the tree is flushed with water to insure adequate distribution of the bacterial cells in the tree. About 24 hours is sufficient for this flushing step.

The *P. syringae* may be used either prophylactically or therapeutically to treat Dutch elm disease in the field.

The antimycotic substance of the *P. syrinage* is produced and a crude preparation thereof is obtained by growing the organism on potato dextrose broth (Difco) adjusted to final concentrations of about 1.5% glucose and about 0.4% casein hydrolysate (Sigma) in standing culture for about 3 days and by extracting the broth with n-butanol, according to the method of D. C. Gross and J. E. De Vay in *Physiol. Plant Pathol.*, 11: 13–28 (1977), which publication is hereby incorporated by reference into this application. In vitro activity against *C. ulmi* of this isolate is demonstrated by the method set forth below in Example 1, except that 5 microliters of the preparation is diluted with an equal volume of water and the diluted preparation is deposited into a well (2 mm diameter×6 mm height) on the plate rather than inoculating the plate with *P. syringae.*

Treatment of Dutch elm disease in the field with the antimycotic substance is accomplished by injecting the substance into an elm using the procedure set forth above except that the aqueous carrier does not contain the nutrients (Dye's salts and glucose). A disadvantage with this method for treating the disease is that retreatment may be required. However, in view of the effectiveness of this antimycotic substance and the discoveries discussed after comparative Example 5, the scope of this invention covers any *P. syringae* forming this antimycotic substance, for the treatment of Dutch elm disease.

The below Examples are illustrative of the method of the present invention and illustrate the unpredictability associated with my discovery of a strain of *P. syringae* that is useful against Dutch elm disease in the field. These Examples shown that the *P. syringae* is useful both prophylactically and therapeutically in the treatment of Dutch elm disease in the field. Briefly, previewing the data set forth below, this data shows that a high level of *C. ulmi* inhibition in vitro cannot be related with any certainty to efficacy in the field. Furthermore, it was unexpectedly discovered in carrying out the fieldwork, that none of the strains of *P. syringae* used appears to have a phytotoxic effect on the elm, that is, they did not produce canker. In view of the prior work of De Vay, for example, U.S. Pat. No. 3,155,585, the likelihood existed that canker would be produced in the elm. Also, it was surprisingly discovered that activity of a strain of *P. syringae* in the greenhouse does not show that the strain will be effective against Dutch elm disease in the field. Specifically, *P. syringae* Comparative Isolate 2 is highly effective as a prophylactic agent against *C. ulmi* when injection into one-year old elm seedlings by gravity flow (the elm seedlings being maintained in a greenhouse), but, as shown in Comparative Example 5B, this strain is ineffective in the field. Finally, as shown in Example 6, the present invention provides a most advantageous method for treating Dutch elm disease since *P. syringae* is capable of living in the elm. Thus, a one treatment procedure is made possible since the microorganism is viable within the tree and exerts a Dutch elm disease controlling effect during the period of viability.

EXAMPLE 1

*P. syringae* NRRL B-12050, an antimycotic substance-forming bacterium, is tested by the following procedure for in vitro activity against *C. ulmi* isolate UT-5F, obtained from N. K. Van Alfen of Utah State University. A 5 microliter sample of the *P. syringae* is taken from a liquid culture containing about $1\times10^8$ colony forming units/ml and is deposited aseptically by loop inoculation on Dye's glucose agar (DGA). DGA plating medium is a modified mineral-salts medium in which 1% glucose is the carbon source and in which Noble agar (1.2%) (Difco) is used. The inoculated plate is incubated at 28° C. in the dark for 27 hours. There is then sprayed onto the surface of the plate using a 3 second spray, an aqueous suspension of the *C. ulmi* having a concentration of $5\times10^6$ spores/ml. A gas-propelled sprayer is used and the sprayer is held about 30 mm from the plate. After the sprayed plate is incubated at room temperature for 2 days, the activity of the *P. syringae* against the *C. ulmi* is determined by the area of the clear inhibition zone surrounding the *P. syringae* colony. The area of the clear inhibition zone is 216 $mm^2$ for the *P. syringae.*

EXAMPLE 2

Following the procedure of Example 1 except that a potato dextrose agar (PDA) plate is used instead of the DGA plating medium, there is found to be a clear inhibition zone having an area of 204 $mm^2$.

COMPARATIVE EXAMPLE 1

Following the procedure of Example 1 except that *P. syringae* Comparative Isolate 1 is used instead of *P. syringae* NRRL B-12050, there is obtained a clear inhibition zone having an area of 0 $m^2$. This strain of *P. syringae* is designated DC 27- in the Montana State University collection and differs from *P. syringae* NRRL B-12050 only that it does not form any antimycotic substance.

COMPARATIVE EXAMPLE 2

Following the procedure of Example 1 except that *P. syringae* Comparative Isolate 2 is used rather than *P. syringae* NRRL B-12050, there is obtained a clear inhibition zone having an area of 452 $mm^2$. This strain of *P. syringae* is designated DC 323+ in the Montana State University collection and forms an antimycotic substance.

EXAMPLE 3

The in vitro activity of *P. syringae* NRRL B-12050 against *C. ulmi* UT-5F on a medium containing elm wood extract is determined by following the procedure set forth in Example 1 except that an elm wood extract-containing medium is used instead of the DGA plating medium. The extract-containing medium is prepared as follows. Elm twigs are harvested from the current year's growth of mature elms, the leaves are excised, and the twigs are cut into 2–5 cm segments. The twig segments are homogenized with an "omni-Mixer" (Sorvall) for 2 minutes in distilled water in the proportion of 1 part twigs (fresh weight in grams) to 5 parts water (ml). The extract is filtered through layers of cheesecloth and is centrifuged at 4° C. for 20 minutes at 4,000 g. The pellet is discarded. The supernatant [11.3 mg (dry weight)/ml] is sterilized, is diluted with distilled water at 4.0, 6.0, 12.5, 20.0 and 100% (vol/vol) and is incorporated into agar (Sigma, 1.3%), pH 7.1. The results are set forth in Table 1. Antimycotic production is calculated in this table and in Table 2 using the equation $y=a+b \ln x$, where y is the area of the zone of inhibition ($mm^2$), x is the concentration of antimycotic (mg/ml), and a and b are constants with values dependent in part upon the type and thickness of the agar.

COMPARATIVE EXAMPLE 3

Following the procedure of Example 3 except that *P. syringae* Comparative Isolate 2 is used rather than *P. syringage* NRRL B-12050, the results set forth in Table 1 are obtained.

EXAMPLE 4

The in vitro activity of *P. syringae* NRRL B-12050 against *C. ulmi* UT-5F on a medium containing expressed cell sap is determined by following the procedure set forth in Example 1 except that an expressed sap-containing medium is used rather than the DGA plating medium. The expressed elm sap-containing medium is prepared by expressing sap from cuttings of new growth from mature elm trees with a plant water status console (Model 3005, Soilmoisture Equipment Corp.). Fluid passing through the stems equal to the volume of the stem is collected with an instrument reading of 5–10 bars, is concentrated about ten times by flash evaporation at 35° C., is freeze dried, and the resulting powder is dried over $P_2O_5$. This powder is then incorporated into a solid medium (1.2% Noble agar, Difco) at 0.01, 0.05, 0.1 and 1.0% (w/v). The results are set forth in Table 2. These results and those in Table 1 show that elm wood extract and expressed xylem sap support the growth of *P. syringae* NRRL B-12050.

COMPARATIVE EXAMPLE 4

Following the procedure of Example 4 except that *P. syringae* Comparative Isolate 2 is used instead of *P. syringae* NRRL B-12050, the results set forth in Table 2 are obtained.

EXAMPLE 5

The effectiveness of *P. syringae* NRRL B-12050 as a protectant against Dutch elm disease in the field is demonstrated in a plot of ten-year old American elms, 6 m in height and 7–10 cm in diameter, and maintained by the U.S. Department of Interior, Washington, D.C. Each of three trees in the plot is inoculated by gravity flow with approximately $10^{11}$ cells of the *P. syringae*, in 1 liter of Dye's salts supplemented with 1% glucose.

TABLE 1

| | Activity against *C. ulmi* on medium containing elm wood extract (units)* | | | | |
|---|---|---|---|---|---|
| | dilution of original elm wood extract | | | | |
| *P. syringae* isolate | $\frac{1}{4}$ | $\frac{1}{6}$ | $\frac{1}{12.5}$ | $\frac{1}{20}$ | $\frac{1}{100}$ |
| NRRL-B-12050 | 7.1 | 7.1 | 0 | 0.8 | 0 |
| Comparative Isolate 2 | 19.6 | 3.1 | 3.1 | 7.1 | 0 |

*One unit of antimycotic activity is defined as that amount of antimycotic which produces a 1 $mm^2$ zone of inhibition in a bioassay against *C. ulmi* (UT-5F).

TABLE 2

| | Activity against *C. ulmi* on medium containing expressed elm sap (units) | | | | |
|---|---|---|---|---|---|
| | Concentration % | | | | |
| *P. syringae* isolate | 0 | 0.01++ | 0.05 | 0.1 | 1.0 |
| NRRL-B-12050 | 0 | 0.8 | 0.8 | 3.1 | 3.1 |
| Comparative Isolate 2 | 0.2 | 4.9 | 15.9 | 9.6 | 4.9 |

++ The concentration of sap that most closely approximates its concentration in elm.

The inoculation is accomplished by drilling 4 to 6 holes, 11 cm in diameter and 2.5 cm deep, into the base of each tree and fitting the holes with a plastic hosing network attached to a 1 liter plastic bottle positioned 1 m above the ground and containing the material to be injected. The inoculation is complete within 12 to 36 hours. About 2 weeks later, each tree is massively challenged with a mixture of aggressive isolates of *C. ulmi* including UT-5F and one isolate from Washington, D.C., by flooding 3 to 4 chisel wounds made 1-5 m from the base of each tree with the *C. ulmi* ($5\times10^4$) and subsequently covering the wounds with clear plastic tape. At least 6 weeks after this second inoculation, each tree is rated visually for symptom expression based on the percentage of the crown showing wilt, necrosis, yellowing or vascular discoloration. The results are set forth in Table 3. In addition to these results, it is surprisingly discovered that this strain of *P. syringae* is not phytotoxic to the elm, that is, it does not cause canker.

As a control, the procedure set forth in the above paragraph is followed for five more elm trees in the plot, except that only *C. ulmi* is injected. The results are set forth in Table 3.

These results show that the *P. syringae* significantly reduces the development of *C. ulmi*, when used prophylactically in the field. Furthermore, evaluation of elm 1A about 56 weeks after inoculation with *C. ulmi* shows continued freedom from the symptoms of Dutch elm disease, this particular elm having been inoculated with the *P. syringae* and *C. ulmi* about one year prior to trees 2A and 3A.

COMPARATIVE EXAMPLE 5

(A) Following the procedure of Example 5 except that *P. syringae* Comparative Isolate 1 is used rather than *P. syringae* NRRL B-12050, and using four more elm trees in the plot, the results set forth in Table 3 are obtained.

TABLE 3

*P. syringae* as a protectant against Dutch elm disease in the field.

| Treatment | Tree | % crown affected[1] | mean[2] |
|---|---|---|---|
| *P. syringae* NRRL-B-12050 | 1A | 0* | |
| | 2A | 2 | |
| | 3A | 80 | 24[a] |
| *C. ulmi* (control) | 1B | 100* | |
| | 2B | 80 | |
| | 3B | 100 | |
| | 4B | 100 | |
| | 5B | 100 | 96[b] |
| *P. syringae* Comparative Isolate 1 | 1C | 100 | |
| | 2C | 75 | |
| | 3C | 100 | |
| | 4C | 50 | 81[b] |
| *P. syringae* Comparative Isolate 2 | 1D | 50* | |
| | 2D | 80 | |
| | 3D | 50 | |

TABLE 3-continued

| *P. syringae* as a protectant against Dutch elm disease in the field. | | | |
|---|---|---|---|
| Treatment | Tree | % crown affected[1] | mean[2] |
| | 4D | 80 | 65[ab] |

[1]All trees were inoculated on June 13, 14, with *P. syringae* except those marked with an asterisk, which were inoculated on July 1 of the previous year. All trees were evaluated on the August 16 following the June 13 inoculation.
[2]Values followed by the same letter are not significantly different (P = 0.05) according to the Newman-Keuls Test.

Comparison of this data with that obtained for *P. syringae* NRRL B-12050 in Example 5 suggests that the ability of *P. syringae* NRRL B-12050 to form an antimycotic substance is related to its activity against Dutch elm disease, since as explained in Comparative Example 1, *P. syringae* Comparative Isolate 1 differs from *P. syringae* NRRL B-12050 only in that it does not form any antimycotic substance. In vivo activity of the antimycotic substance is discussed above.

(B) Following the procedure of Example 5 except that *P. syringae* Comparative Isolate 2 is used rather than *P. syringae* NRRL B-12050, and using four more elm trees in the plot, the results set forth in Table 3 are obtained. Furthermore, it is unexpectedly discovered that neither of the strains used in this comparative example is phytotoxic to the elm since neither causes canker.

Dialysis and TLC of the antimycotic substance formed by *P. syringae* Comparative Isolate 2 and of the antimycotic substance formed by *P. syringae* NRRL B-12050 shows that these two antimycotic substances are different. Specifically, this testing shows the presence of three compounds in the substance formed by *P. syringae* NRRL B-12050 and the presence of two compounds in the substance formed by *P. syringae* Comparative Isolate 2, with the additional compound in the former substance not passing through the dialysis membrane. In vitro testing of a crude isolate of this additional compound, generally using the procedure of Example 1, shows activity against *C. ulmi.* In vitro testing of a crude isolate of the other two compounds in combination, and of a crude isolate of the material formed by *P. syringae* Comparative Isolate 2 in combination, also shows activity against *C. ulmi.*

Comparison of the TLC of the former substance against the TLC of the antimycotic substance formed by De Vay's B-3 strain of *P. syringae* shows by $R_f$ values that the components of the substances are completely different. This difference may explain the apparent lack of phytotoxicity of *P. syringae* NRRL B-12050 in the elm.

EXAMPLE 6

The therapeutic effect of *P. syringae* NRRL B-12050 against Dutch elm disease in the field is demonstrated as follows. Elms in Sioux Falls, S. Dak. (40–82 cm d.b.h.), showing about 5–50% crown destruction due to Dutch elm disease in the early summer, are each inoculated with about $5\times10^{11}$ cells of the *P. syringae* in 60 liters of water containing 4 liters of Dye's salts supplemented with 1% glucose. The inoculation is accomplished via 20–30 T's attached to a hosing network and inserted into the root flares 20 cm below the ground, with the injection being carried out at 10 lbs. pressure for 24 hours, followed by flushing each tree with water for 24 hours to insure adequate distribution of the bacteria within the tree. On August 20 (41 days to 1 year and 67 days after injection) each tree is evaluated for the development of crown symptoms. The results are shown in Table 4.

A control is provided by comparing an untreated tree of the same relative size that shows virtually the same degree of disease severity at the time of the inoculation. The results for the control trees are shown in Table 4.

The data in Table 4 shows that nearly 50% of the trees treated with the *P. syringae* do not progress in symptom development, and that there is generally a substantially reduced symptom development in those treated trees showing a progression in symptom development when compared with the controls. Furthermore, in one treated tree, sympton expression is remitted for 60 weeks (two growing seasons), whereas the control tree succumbed to Dutch elm disease. 60 weeks after inoculation, an antimycotic fluorescent pseudomonad is readily recovered from trunk borings of the treated tree, thus demonstrating the ability of the *P. syringae* to live in the tree and to survive through winter.

TABLE 4

Therapeutic treatment of diseased elms in the field.

| Tree diameter (cm) | % crown infected prior to injection with *P. syringae* NRRL-B-12050 | % crown infected 41 days to 1 year and 67 days after injection | % change |
|---|---|---|---|
| 77 (treated) | 30 | 45 (62 days) | 50 |
| 62 (control) | 30 | 90 | 200 |
| 45 (treated) | 35 | 50 (60 days) | 43 |
| 50 (control) | 20 | 100 | 400 |
| 42 (treated) | 20 | 20 (60 days) | 0 |
| 40 (control) | 20 | 80 | 300 |
| 37 (treated) | 20 | 100 (59 days) | 400[2] |
| 40 (control) | 10 | 90 | 800 |
| 40 (treated) | 10 | 10 (1 year and | 0 |
| 40 (control) | 10 | 100 67 days) | 900 |
| 50 (treated) | 5 | 5 (56 days) | 0 |
| 52 (control) | 5 | 25 | 400 |
| 40 (treated) | 20 | 40 (52 days) | 100 |
| 35 (control) | 20 | 60 | 200 |
| 50 (treated) | 5 | 5 (52 days) | 0[3] |
| 45 (control) | 10 | 40 | 300 |
| 36 (treated) | 30 | 60 (49 days) | 100 |
| 35 (control) | 20 | 60 | 200 |
| 50 (treated) | 15 | 15 (49 days) | 0 |
| 45 (control) | 10 | 60 | 500 |
| 44 (treated) | 5 | 5 (46 days) | 0 |
| 52 (control) | 5 | 25 | 400 |
| 43 (treated) | 10 | 15 (42 days) | 50 |
| 40 (control) | 25 | 50 | 100 |
| 36 (treated) | 15 | 20 (42 days) | 33 |
| 40 (control) | 15 | 100 | 565 |
| 36 (treated) | 10 | 40 (41 days) | 300 |
| 45 (control) | 10 | 40 | 300 |
| 120[1] (treated) | 45 | 45 (53 days) | 0[3] |
| 90[1] (control) | 55 | 90 | 64 |
| 90[1] (treated) | 50 | 55 (53 days) | 10[3] |
| 90[1] (control) | 25 | 75 | 200 |

[1]Rhode Island elms
[2]Died
[3]Trees expressing new growth late in the season on limbs and branches previously showing symptoms of Dutch elm disease.

EXAMPLE 7

Following the procedure of Example 6 except that the diseased elms treated were located in Little Compton, Rhode Island, and selecting controls in the manner explained in Example 6, the results set forth in Table 4 are obtained.

APPLICABILITY

This invention is useful for the control of Dutch elm disease.

I claim:

1. A method of treating Dutch elm disease comprising applying a Dutch elm disease-controlling amount of *P. syringae* NRRL B-12050 to an elm tree.

2. The method of claim 1, wherein said applying is by injection into the elm tree.

3. The method of claim 2 wherein said amount is in the range of about $10^8$ to $10^{11}$ total cells.

4. The method of claim 2 wherein said amount is about $10^8$ to $10^9$ living cells.

5. The method of claim 2 wherein the *P. syringae* is injected in an aqueous vehicle containing nutrients for the *P. syringae*.

6. The method of claim 2 wherein the injection is by gravity flow.

7. The method of claim 2 wherein the injection is at a pressure in excess of the force of gravity.

8. The method of claim 7 wherein the injection is at about 10 lbs. pressure.

9. The method of claim 7 wherein the elm is flushed with water after the injection step, whereby adequate distribution of said *P. syringae* within the tree is provided.

10. The method of claim 2, wherein the elm tree is infected with Dutch elm disease.

11. The method of claim 2, wherein the elm tree is uninfected with Dutch elm disease.

12. A method of treating Dutch elm disease comprising applying an antimycotic substance-forming strain of *P. syringae* to an elm tree in a Dutch elm disease-controlling amount; said antimycotic substance being that produced by cultivating *P. syringae* NRRL B-12050 in suitable aqueous nutrient medium and isolating said antimycotic substance therefrom by extracting with n-butanol.

13. The method of claim 12, wherein the elm tree is infected with Dutch elm disease.

14. The method of claim 12, wherein the elm tree is uninfected with Dutch elm disease.

15. The method of claim 12, wherein said applying is by injection into the elm tree.

16. The method of claim 15, wherein said amount is in the range of about $10^8$ to $10^{11}$ total cells.

17. The method of claim 15, wherein said amount is about $10^8$ to $10^9$ living cells.

18. The method of claim 15, wherein the *P. syringae* is injected in an aqueous vehicle containing nutrients for the *P. syringae*.

19. The method of claim 15, wherein the elm is flushed with water after the injection step, whereby adequate distribution of said *P. syringae* within the tree is provided.

* * * * *